(12) United States Patent
McGall et al.

(10) Patent No.: US 6,881,836 B2
(45) Date of Patent: Apr. 19, 2005

(54) PHOTOCLEAVABLE PROTECTING GROUPS AND METHODS FOR THEIR USE

(75) Inventors: Glenn H. McGall, Mountain View, CA (US); Ngo Q. Nam, Campbell, CA (US); Richard P. Rava, San Jose, CA (US)

(73) Assignee: Affymetrix, Inc, Santa Clara, CA (US)

( * ) Notice: Subject to any disclaimer, the term of this patent is extended or adjusted under 35 U.S.C. 154(b) by 82 days.

(21) Appl. No.: 10/348,917

(22) Filed: Jan. 22, 2003

(65) Prior Publication Data

US 2003/0144499 A1 Jul. 31, 2003

Related U.S. Application Data

(60) Division of application No. 09/525,045, filed on Mar. 14, 2000, now Pat. No. 6,566,515, which is a continuation of application No. 08/812,005, filed on Mar. 5, 1997, now Pat. No. 6,147,205, which is a continuation-in-part of application No. 08/630,148, filed on Apr. 10, 1996, now Pat. No. 6,022,963.

(60) Provisional application No. 60/008,684, filed on Dec. 15, 1995.

(51) Int. Cl.[7] .............................................. C07H 21/00
(52) U.S. Cl. ................... 536/25.3; 536/124; 536/25.31; 536/25.32; 536/25.33; 536/25.34; 436/518; 514/19; 514/275; 514/278; 435/6; 435/7.92; 435/7.94
(58) Field of Search .......................... 536/25.3, 25.31, 536/25.32, 25.33, 25.34; 436/518; 514/19, 215, 278; 435/6, 7.92, 7.94

(56) References Cited

U.S. PATENT DOCUMENTS 4,242,974 A 1/1981 Beckerman (Continued)

FOREIGN PATENT DOCUMENTS

WO WO-89/10977 11/1989 ............ C12Q/1/68

(Continued)

OTHER PUBLICATIONS

Adams, S..R. ,et al. ,"Controlling cell chemistry with caged compounds", *Ann. Rev. Physiol.*, 55, (1993),pp. 755–784.

(Continued)

*Primary Examiner*—James Wilson
*Assistant Examiner*—Devesh Khare
(74) *Attorney, Agent, or Firm*—Thomas E. Malone; Philip L. McGarrigle; Schwegman, Lundberg, Woessner & kluth, P.A.

(57) ABSTRACT

Novel compounds are provided which are useful as linking groups in chemical synthesis, preferably in the solid phase synthesis of oligonucleotides and polypeptides. These compounds are generally photolabile and comprise protecting groups which can be removed by photolysis to unmask a reactive group. The protecting group has the general formula Ar—C($R_1$)($R_2$)—O—C(O)— wherein:

Ar is an optionally substituted fused polycyclic aryl or heteroaromatic group or a vinylogous derivative thereof;

$R_1$ and R2 are independently H, optionally substituted alkyl, alkenyl or alkynyl, optionally substituted aryl or optionally substituted heteroaromatic, or a vinylogous derivative of the foregoing; and X is a leaving group, a chemical fragment linked to Ar—C($R_1$)($R_2$)—O—C(O)— via a heteroatom, or a solid support; provided that when Ar is 1-pyrenyl and $R_1$ and $R_2$ are H, X is not linked to Ar—C($R_1$)($R_2$)—O—C(O)— via a nitrogen atom. Preferred embodiments are those in which Ar is a fused polycyclic aromatic hydrocarbon and in which the substituents on Ar, $R_1$ and $R_2$ are electron donating groups. A particularly preferred protecting group is the "PYMOC" protecting group, pyrenylmethyloxycarbonyl, where Ar is pyrenyl and $R_1$ and $R_2$ are H.

Also provided is a method of forming, from component molecules, a plurality of compounds on a support, each compound occupying a separate predefined region of the support, using the protected compounds described above.

11 Claims, 4 Drawing Sheets

U.S. PATENT DOCUMENTS

| | | | |
|---|---|---|---|
| 5,143,854 A | 9/1992 | Pirrung et al. | 436/518 |
| 5,200,051 A | 4/1993 | Cozzette et al. | 204/403 |
| 5,212,050 A | 5/1993 | Mier et al. | 430/320 |
| 5,215,899 A | 6/1993 | Dattagupta | |
| 5,242,974 A | 9/1993 | Holmes | 525/54.11 |
| 5,384,261 A | 1/1995 | Winkler et al. | 436/518 |
| 5,412,087 A | 5/1995 | McGall et al. | 536/24.3 |
| 5,413,854 A | 5/1995 | Sato | |
| 5,420,328 A | 5/1995 | Campbell | |
| 5,424,186 A | 6/1995 | Fodor et al. | |
| 5,430,136 A | 7/1995 | Urdea et al. | |
| 5,445,934 A | 8/1995 | Fodor et al. | 435/6 |
| 5,489,678 A | 2/1996 | Fodor et al. | 536/22.1 |
| 5,503,805 A | 4/1996 | Sugarman et al. | |
| 5,541,061 A | 7/1996 | Fodor et al. | 435/6 |
| 5,580,697 A | 12/1996 | Keana et al. | 430/296 |
| 5,582,955 A | 12/1996 | Keana et al. | 430/296 |
| 5,639,603 A | 6/1997 | Dower et al. | 435/6 |
| 5,677,195 A | 10/1997 | Winkler et al. | 436/518 |
| 5,700,637 A | 12/1997 | Southern | 435/6 |
| 5,770,358 A | 6/1998 | Dower et al. | 435/6 |
| 5,830,539 A | 11/1998 | Yan et al. | 427/551 |
| 5,959,098 A | 9/1999 | Goldberg et al. | 536/25.3 |
| 6,022,597 A | 2/2000 | Yan et al. | 427/558 |
| 6,022,963 A * | 2/2000 | McGall et al. | 536/25.3 |
| 6,054,504 A | 4/2000 | Dalla Riva Toma | 523/122 |
| 6,147,205 A | 11/2000 | McGall et al. | 536/25.31 |

FOREIGN PATENT DOCUMENTS

| | | | |
|---|---|---|---|
| WO | WO-90/15070 | 12/1990 | C07K/1/04 |
| WO | WO-92/10092 | 6/1992 | A01N/1/02 |
| WO | WO-92/12492 | 7/1992 | |
| WO | WO-93/06121 | 4/1993 | |

OTHER PUBLICATIONS

Ajayaghosh,et al. ,"Polymer–supported synthesis of protected peptide segments on a photosensitive o–nitro (alpha–methyl) bromobenzyl resin", *Tetrahedron Letters*, 44 (21), (1988),pp. 6661–6666.

Amit, B..,et al. ,"Photosensitive protecting groups of amino sugars and their use in glycoside synthesis. 2–nitrobenzyloxycarbonylamino and 6–nitroveratryloxycarbonylamino derivatives", *J. Org. Chem.*, 39, (1974),pp. 192–196.

Atherton, E..,"Table of Contents", *Solid Phase Peptide Synthesis: A Practical Approach*, New York: IRL Press at Oxford University Press,(1989),pp. vii–ix.

Bos,et al. ,"Amino–acid substitutions at condon 13 of the N–ras oncogene in human acute myeloid leukamia", *Nature*, 315, (1985),pp. 726–730.

Corrie, J..E. ,et al. ,"Chapter 5: Caged Nucleotides and Neurotransmitters", *In: Biological Applications of Photochemical Switches, vol. 2 (Bioorganic Photochemistry Series)*, Morrison, H. Ed., J. Wiley & Sons,(1993),pp. 243–305.

Crooke, S..T. ,et al. ,"Table of Contents", *Antisense Research and Applications*, Crooke, S.T , et al., Ed., CRC Press, Boca Raton, FL,(1993),4 pages.

Elder, J..K. ,"Analysis of DNA oligonucleotide hybridization data by maximum entropy", *In: Maximum Entropy and Bayesian Methods—Proceedings of the Twelfth International Workshop*, Mohammad–Dhafari and Demoment, G., Eds., Kluwer Academic Publishers, Paris, France,(1993),pp. 363–371.

Fodor,et al. ,"Light–directed, spatialyl addressable parallel chemical synthesis", *Science*, 251, (1991),pp. 767–773.

Fourrey,et al. ,"1,1–bis–(4–methoxyphenyl)–1'–pyrenyl methyl (bmpm): A New Fluorescent 5' Protecting Group for the Purification of Unmodified and Modified Oligonucleotides", *Tetrahedron Letters*, 28(43), (1987),pp. 5157–5160.

Furuta,et al. ,"Direct Esterification of Phosphates with Various Halides and Its Application to Synthesis of cAMP Alkyl Triesters", *J. Chem Soc. Perkin Trans., 1*, (1993),pp. 3139–3142.

Furuta,et al. ,"New Photochemically Labile Protecting Group for Phosphates", *Chemistry Letters*, (1993),pp. 1179–1182.

Gallop,et al. ,"Applications of Combinatorial Technologies to Drug Delivery. 1. Background and Peptide Combinatorial Libraries", *J. Med. Chem.*, 37 (9), (1994),pp. 1233–1251.

Geysen,et al. ,"Strategies for Epitope Analysis Using Peptide Synthesis", *J. Immunol. Meth.*, 102, (1987),pp. 259–274.

Givens, R..S. ,et al. ,"Photochemistry of Phosphates Esters", *Chem. Rev.*, 93, (1993),pp. 55–66.

Gordon,et al. ,"Applications of Combinatorial Technologies to Drug Discovery. 2. Combinatorial Organic Synthesis, Library Screening Strategies, and Future Directions", *J. Med. Chem.*, 37(10), (1994),pp. 1385–1401.

Hammer,et al. ,"Practical Approach to Solid–Phase Synthesis of c–terminal Peptide Amides Under Mild Conditions Based on a Photolysable Anchoring Linkage", *Int. J. Peptide Protein Res.*, 36, (1990),pp. 31–45.

Hochgeschwender,et al. ,"Preferential Expression of a Defined T–cell Receptor Beta–chain gene in Hapten–specific Cytotoxic T–cell Clones", *Nature*, 322, (1986),pp. 376–378.

Holmes,et al. ,"Development of a New Photo–removable Protecting Group for the Amino and Carboxyl Groups of Amino Acids", *In: Peptides: Chemistry, Structure, and Biology*, vol. 13, Hodges, R.S., et al., Eds., Escom Science Publishers (Proceeding of the 13th American Peptide Symposium: Jun. 20–25, 1993, Edmonton, Alberta, Canada), (1994),pp. 110–112.

Houghten,et al. ,"Generation and use of synthetic peptide combinatorial libraries for basic research and drug delivery", *Nature*, 354, (1991),pp. 84–86.

Iwamura,et al. ,"1–(alpha–diazbenzyl) pyrene: a reagent for photolabile and fluorescent protection of carboxyl groups of amino acids and peptides", *Synlett*, (1991),pp. 35–36.

Iwamura,et al. ,"1–pyrenylmethyl esters, photolabile protecting groups for carboxylic acids", *Tetrahedron Letters*, 28(6), (1987),pp. 679–682.

Iwamura,et al. ,"Photoreactivity of 1–pyrenylmethy esters. Dependence on the structure of the carboxylic acid moieties and the nature of the excited states", *Chemistry Letters*, (1987),pp. 1729–1732.

Lam,"A new type of synthetic peptide library for identifying ligand–binding activity", *Nature*, 354, (1991),pp. 82–84.

Lloyd–Williams,et al. ,"Convergent solid–phase peptide synthesis", *Tetrahedron Letters*, 49(48), (1993),pp. 11065–11133.

McGall, G..H. ,"Chapter 2: The fabrication of high density oligonucleotides arrays for hybridization–based sequence analysis", *In: Biochip Arrays and Integrated Devices for Clinical Diagnostics*, IBC Library Series, Based on the edited and updated transcripts from IBC's International Conference held in San Diego, CA,(Mar. 5–6, 1997),pp. 2.1–2.33.

Okada, S.., et al., "(1–pyrenyl)methyl carbamates for fluorescent "caged" amino acids and peptides", *Photochemistry and Photobiology*, 61(5), (1995), pp. 431–434.

Patchornik, "Photosensitive Protecting Groups", *J. Am. Chem. Soc.*, 92, (1970), pp. 6333–6335.

Pease, Ann.C., "Light–generated oligonucleotide arrays for rapid DNA sequence analysis", *PNAS*, 91, (May, 1994), 5022–5026.

Pillai, V..N., "Photolytic deprotection and activation of functional groups", *Organic Photochemistry*, vol. 9, A. Padwa, Ed., Marcel Dekker, (1987), pp. 225–323.

Pillai, V..N., "Photoremovable protecting groups in organic synthesis", *Synthesis, International Journal of Methods in Synthetic Organic Chemistry*, Schill, G., et al., Eds., (1980), pp. 1–26.

Rich, et al., "Preparation of a new o–nitorbenzyl resin for solid–phase synthesis of tertbutyloxycarbonyl–protected peptide acids", *J. Amer. Chem. Soc.*, 97(6), (1974), pp. 1575–3261.

Sanghvi, Y..S., et al., "Carbohydrate Modifications in Antisense Research", *ACS Symposium Series # 580 0097*, Table of Contents, Sanghvi, Y.S., et al., Eds., American Chemical Society, Washington, D.C., (1994), pp. v–vi.

Southern, et al., "Analyzing and comparing nucleic acid sequences by hybridization to arrays of oligonuceotides: evaluation using experimental models", *Genomics*, 13, (1992), pp. 1008–1017.

Verlann–De Vries, et al., "A dot–blot screening procedure for mutated ras oncogenes using synthetic oligodeoxynucleotides", *Gene*, 50, (1986), pp. 313–320.

Wang, et al., "Solid phase synthesis of protected peptides via photolytic cleavage of the alpha–methylphenacy ester anchoring linkage", *J. Org. Chem.*, 41(20), (1976), pp. 3258–3261.

Yankee, et al., "Photosensitive Protecting Groups", *Journal of the American Society*, 92 (21), (1970), pp. 6333–6335.

Zehavi, U.., "Applications of photosensitive protecting groups in carbohydrate chemistry", *Adv. Carbohydrate Chem. Biochem.*, 46, (1988), pp. 179–204.

* cited by examiner

Benzyl Photo-cleavable Protecting Groups

General:

$R_1$, $R_2$ = H, alkyl, substituted aromatic hydrocarbon

X = O, S, N-alkyl, $CH_2$, $CH_2$-$CH_2$, CH=CH

Y = alkyl, substituted aromatic, electron-donating group

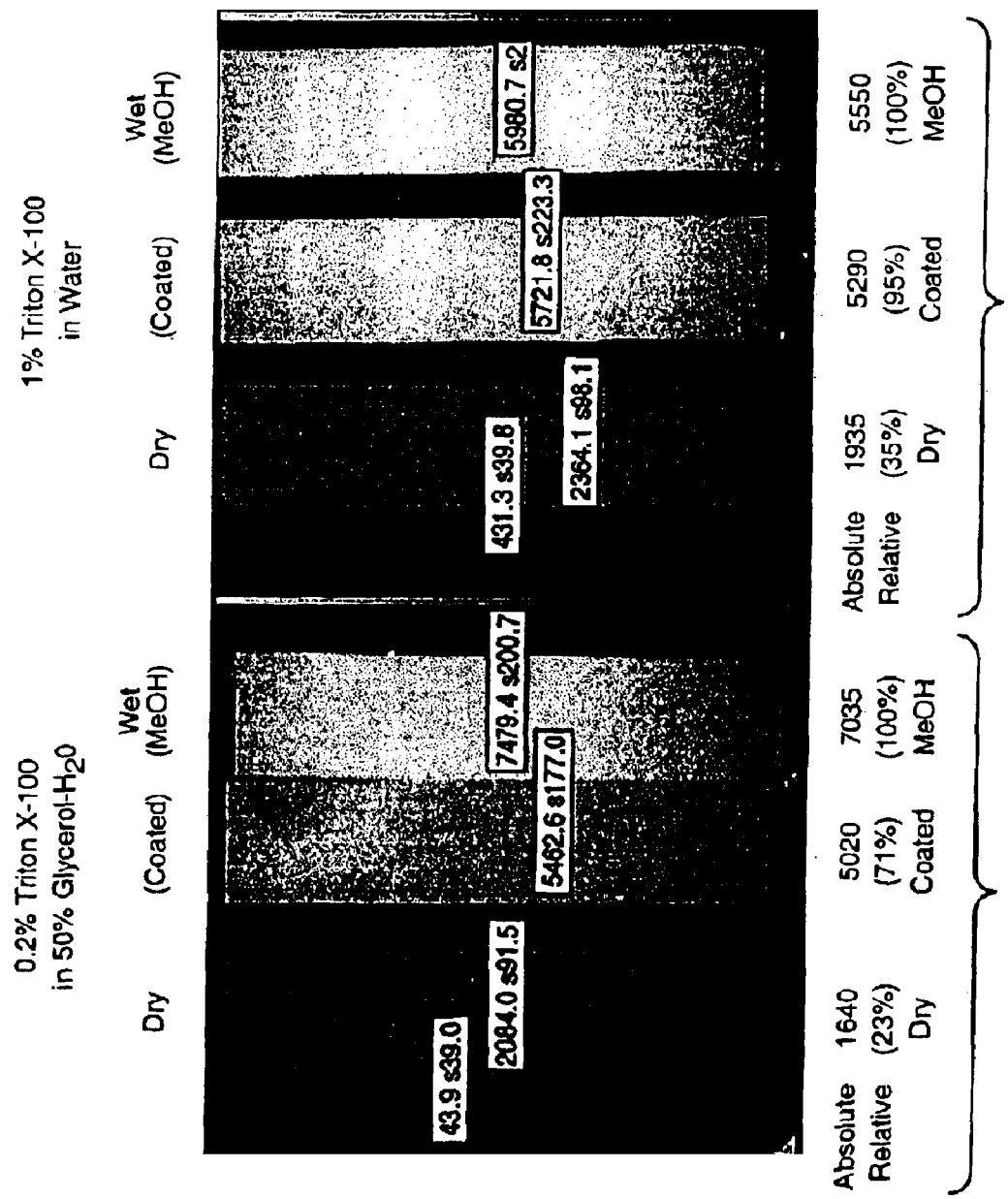

SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Decanucleotide used in a test array
<220> FEATURE:
<221> NAME/KEY: misc_feature
<222> LOCATION: (1)...(10)
<223> OTHER INFORMATION: n = A,T,C or G

<400> SEQUENCE: 1 tncngtncan                                                          10

<210> SEQ ID NO 2
<211> LENGTH: 22
<212> TYPE: DNA
<213> ORGANISM: Artificial Sequence
<220> FEATURE:

-continued

```
<223>  OTHER INFORMATION: A complementary fluoresein-labelled
       oligonucleotide "target"

<400>  SEQUENCE: 2 actggactga acggtaatgc ac                                            22
```

PHOTOCLEAVABLE PROTECTING GROUPS AND METHODS FOR THEIR USE

CROSS REFERENCE TO RELATED APPLICATIONS

The present application is a division of U.S. patent application Ser. No. 09/525,045, filed on Mar. 14, 2000, now U.S. Pat. No. 6,566,515; which is a continuation of U.S. patent application Ser. No. 08/812,005, filed on Mar. 5, 1997, now U.S. Pat. No. 6,147,205; which is a continuation-in-part of U.S. patent application Ser. No. 08/630,148, filed Apr. 10, 1996, now U.S. Pat. No. 6,022,963; which is a regular application of Provisional Patent Application No. 60/008,684, filed Dec. 15, 1995, all of which are incorporated herein by reference.

The present invention was made with U.S. Government support under ATP Grant No. 70NANB5H1031, and the government may have certain rights in the invention.

BACKGROUND OF THE INVENTION

The present invention relates to the area of chemical synthesis. More particularly, this invention relates to photolabile compounds, reagents for preparing the same and methods for their use as photocleavable linkers and protecting groups, particularly in the synthesis of high density molecular arrays on solid supports.

The use of a photolabile molecule as a linker to couple molecules to solid supports and to facilitate the subsequent cleavage reaction has received considerable attention during the last two decades. Photolysis offers a mild method of cleavage which complements traditional acidic or basic cleavage techniques. See, e.g., Lloyd-Williams et al. (1993) *Tetrahedron* 49:11065–11133. The rapidly growing field of combinatorial organic synthesis (see, e.g., Gallop et al. (1994) *J. Med. Chem.* 37:1233–1251; and Gordon et al. (1994) *J. Med. Chem.* 37:1385–1401) involving libraries of peptides and small molecules has markedly renewed interest in the use of photolabile linkers for the release of both ligands and tagging molecules.

A variety of ortho-benzyl compounds as photolabile protecting groups have been used in the course of optimizing the photolithographic synthesis of both peptides (see Fodor et al. (1994) *Science* 251:767–773) and oligonucleotides (see Pease et al. *Proc. Natl. Acad. Sci. USA* 91:5022–5026). See PCT patent publication Nos. WO 90/15070, WO 92/10092, and WO 94/10128; see also U.S. patent application Ser. No. 07/971,181, filed 2 Nov. 1992, and Ser. No. 08/310,510, filed Sep. 22, 1994; Holmes et al. (1994) in *Peptides: Chemistry, Structure and Biology* (*Proceedings of the 13th American Peptide Symposium*); Hodges et al. Eds.; ESCOM: Leiden; pp. 110–12, each of these references is incorporated herein by reference for all purposes. Examples of these compounds included the 6-nitroveratryl derived protecting groups, which incorporate two additional alkoxy groups into the benzene ring. Introduction of an α-methyl onto the benzylic carbon facilitated the photolytic cleavage with >350 nm UV light and resulted in the formation of a nitroso-ketone.

Photocleavable protecting groups and linkers should be stable to a variety of reagents (e.g., piperidine, TFA, and the like); be rapidly cleaved under mild conditions; and not generate highly reactive byproducts. The present invention provides such protecting groups and methods for their use in synthesizing high density molecular arrays.

SUMMARY OF THE INVENTION

According to a first aspect of the invention, novel compounds are provided which are useful for providing protecting groups in chemical synthesis, preferably in the solid phase synthesis of oligonucleotides and polypeptides. These compounds are generally photolabile and comprise protecting groups which can be removed by photolysis to unmask a reactive group. The compounds have the general formula Ar—C($R_1$)($R_2$)—O—C(O)—X, wherein:

Ar is an optionally substituted fused polycyclic aryl or heteroaromatic group or a vinylogous derivative thereof;

$R_1$ and $R_2$ are independently H, optionally substituted alkyl, alkenyl or alkynyl, optionally substituted aryl or optionally substituted heteroaromatic, or a vinylogous derivative of the foregoing; and X is a leaving group, a chemical fragment linked to Ar—C($R_1$)($R_2$)—O—C(O)— via a heteroatom, or a solid support; provided that when Ar is 1-pyrenyl and $R_1$=$R_2$=H, X is not linked to Ar—C($R_1$)($R_2$)—O—C(O)— via a nitrogen atom. Preferred embodiments are those in which Ar is a fused polycyclic aromatic hydrocarbon and in which the substituents on Ar, $R_1$ and $R_2$ are electron donating groups. Particularly preferred protecting groups are the "PYMOC" protecting group, pyrenylmethyloxycarbonyl, where Ar=1-pyrenyl and $R_1$=$R_2$=H, and the "ANMOC" protecting group, anthracenylmethyloxycarbonyl, where Ar=anthracenyl and $R_1$=$R_2$=H. Methods are provided for preparing these compounds This invention also provides reagents of the molecular formula Ar—C($R_1$)($R_2$)—O—C(O)—X, where Ar, $R_1$, and $R_2$ have the meanings ascribed above, for incorporating the protecting group into the molecule desired to be protected.

Another aspect of this invention provides a method of attaching a molecule with a reactive site to a support comprising the steps of:

(a) providing a support with a reactive site;

(b) binding a molecule to the reactive site, the molecule comprising a masked reactive site attached to a photolabile protecting group of the formula Ar—C($R_1$)($R_2$)—O—C(O)—, wherein:

Ar is an optionally substituted fused polycyclic aryl or heteroaromatic group or a vinylogously substituted derivative of the foregoing;

$R_1$ and $R_2$ are independently H, optionally substituted alkyl, alkenyl or alkynyl, or optionally substituted aryl or heteroaromatic group or a vinylogously substituted derivative of the foregoing;

to produce a derivatized support having immobilized thereon the molecule attached to the photolabile protecting group; and (c) removing the photolabile protecting group to provide a derivatized support comprising the molecule with an unmasked reactive site immobilized thereon.

A related aspect of this invention provides a method of forming, from component molecules, a plurality of compounds on a support, each compound occupying a separate predefined region of the support, said method comprising the steps of:

(a) activating a region of the support;

(b) binding a molecule to the region, said molecule comprising a masked reactive site linked to a photolabile protecting group of the formula Ar—C($R_1$)($R_2$)—O—C(O)—, wherein:

Ar is an optionally substituted fused polycyclic aryl or heteroaromatic group or a vinylogously substituted derivative of the foregoing;

$R_1$ and $R_2$ are independently H, optionally substituted alkyl, alkenyl or alkynyl, or optionally substituted aryl or heteroaromatic group or a vinylogously substituted derivative of the foregoing;

(c) repeating steps (a) and (b) on other regions of the support whereby each of said other regions has bound thereto another molecule comprising a masked reactive site linked to the photolabile protecting group, wherein said another molecule may be the same or different from that used in step (b);

(d) removing the photolabile protecting group from one of the molecules bound to one of the regions of the support to provide a region bearing a molecule with an unmasked reactive site;

(e) binding an additional molecule to the molecule with an unmasked reactive site;

(f) repeating steps (d) and (e) on regions of the support until a desired plurality of compounds is formed from the component molecules, each compound occupying separate regions of the support.

The present invention also provides methods of performing chemical reactions on a surface, by providing at least one chemical reactant on the surface, and applying a coating to the surface. The coating provides an environment that is favorable to reaction of the chemical reactant. In a more preferred aspect, the invention provides a method of activating a functional group on a surface that is protected with a protecting group of the invention. The method involves applying a nucleophilic coating to the surface, and exposing the surface to light to remove the protecting group.

The methods and compositions described herein find particular utility in the synthesis of high density arrays of compounds, and particularly nucleic acids, on solid supports.

BRIEF DESCRIPTION OF THE DRAWINGS

FIG. 4 illustrates fluorescent scans of substrates subjected to dry front-side exposure, coated front-side exposure and wet exposure (water/MeOH in a flow cell). Two coatings (0.1% Triton X-100/$H_2O$ and 0.2% Triton X-100/50% glycerol/$H_2O$) were tested and the results are shown in panels A and B, respectively.

DESCRIPTION OF THE PREFERRED EMBODIMENT

Figure 1:
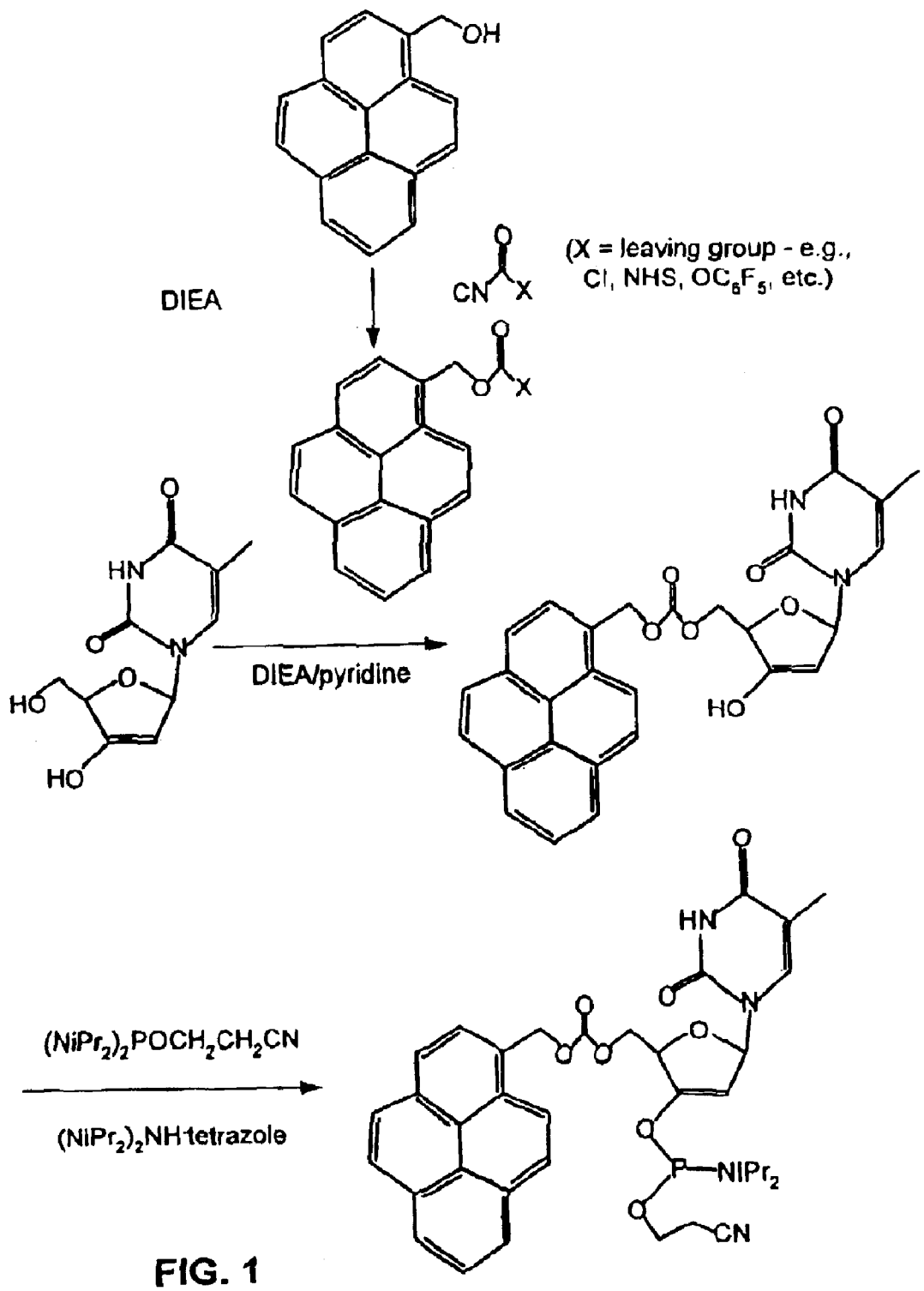
FIGS. 1 and 2 show syntheses of 5'-O-pyrenylmethyloxycarbonyl ("PYMOC") protected deoxyribonucleoside 3'-O-cyanoethylphosphoramidites in a suitable form for coupling to a support.

The following definitions are set forth to illustrate and define the meaning and scope of the various terms used to describe the invention herein.

The term "alkyl" refers to a branched or straight chain acyclic, monovalent saturated hydrocarbon radical of one to twenty carbon atoms.

The term "alkenyl" refers to an unsaturated hydrocarbon radical which contains at least one carbon-carbon double bond and includes straight chain, branched chain and cyclic radicals.

The term "alkynyl" refers to an unsaturated hydrocarbon radical which contains at least one carbon-carbon triple bond and includes straight chain, branched chain and cyclic radicals.

The term "aryl" refers to an aromatic monovalent carbocyclic radical having a single ring (e.g., phenyl) or two condensed rings (e.g., naphthyl), which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Alternatively, two adjacent positions of the aromatic ring may be substituted with a methylenedioxy or ethylenedioxy group. Typically, electron-donating substituents are preferred.

The term "heteroaromatic" refers to an aromatic monovalent mono- or poly-cyclic radical having at least one heteroatom within the ring, e.g., nitrogen, oxygen or sulfur, wherein the aromatic ring can optionally be mono-, di- or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. For example, typical heteroaryl groups with one or more nitrogen atoms are tetrazoyl, pyridyl (e.g., 4-pyridyl, 3-pyridyl, 2-pyridyl), pyrrolyl (e.g., 2-pyrrolyl, 2-(N-alkyl)pyrrolyl), pyridazinyl, quinolyl (e.g. 2-quinolyl, 3-quinolyl etc.), imidazolyl, isoquinolyl, pyrazolyl, pyrazinyl, pyrimidinyl, pyridonyl or pyridazinonyl; typical oxygen heteroaryl radicals with an oxygen atom are 2-furyl, 3-furyl or benzofuranyl; typical sulfur heteroaryl radicals are thienyl, and benzothienyl; typical mixed heteroatom heteroaryl radicals are furazanyl and phenothiazinyl. Further the term also includes instances where a heteroatom within the ring has been oxidized, such as, for example, to form an N-oxide or sulfone.

The term "optionally substituted" refers to the presence or lack thereof of a substituent on the group being defined. When substitution is present the group may be mono-, di- or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Typically, electron-donating substituents such as alkyl, lower-alkyl, cycloalkyl, hydroxylower-alkyl, aminolower-alkyl, hydroxyl, thiol, amino, halo, lower-alkylthio, lower-alkoxy, mono-lower-alkylamino and di-lower-alkylamino are preferred.

The term "electron donating group" refers to a radical group that has a lesser affinity for electrons than a hydrogen atom would if it occupied the same position in the molecule. For example, typical electron donating groups are hydroxy, alkoxy (e.g. methoxy), amino, alkylamino and dialkylamin0.

The term "leaving group" means a group capable of being displaced by a nucleophile in a chemical reaction, for example halo, nitrophenoxy, pentafluorophenoxy, alkyl sulfonates (e.g., methanesulfonate), aryl sulfonates, phosphates, sulfonic acid, sulfonic acid salts, and the like.

"Activating group" refers to those groups which, when attached to a particular functional group or reactive site, render that site more reactive toward covalent bond formation with a second functional group or reactive site. For example, the group of activating groups which can be used in the place of a hydroxyl group include —O(CO)Cl; —OCH$_2$Cl; —O(CO)OAr, where Ar is an aromatic group, preferably, a p-nitrophenyl group; —O(CO)(ONHS); and the like. The group of activating groups which are useful for a carboxylic acid include simple ester groups and anhydrides. The ester groups include alkyl, aryl and alkenyl esters and in particular such groups as 4-nitrophenyl, N-hydroxysuccinimide and pentafluorophenol. Other activating groups are known to those of skill in the art.

"Chemical library" or "array" is an intentionally created collection of differing molecules which can be prepared either synthetically or biosynthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Predefined region" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct compound is synthesized smaller than about 1 cm$^2$ or less than 1 mm$^2$. Within these regions, the molecule synthesized therein is preferably synthesized in a substantially pure form. In additional embodiments, a predefined region can be achieved by physically separating the regions (i.e., beads, resins, gels, etc.) into wells, trays, etc.

"Solid support", "support", and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by reference to the examples hereinbelow. However, other equivalent separation or isolation procedures can, of course, also be used.

A "channel block" is a material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

This invention provides novel compounds which are useful for providing protecting groups in chemical synthesis, preferably in the solid phase synthesis of oligonucleotides and polypeptides and high density arrays thereof. These compounds are generally photolabile and comprise protecting groups which can be removed by photolysis to unmask a reactive group. The compounds have the general formula Ar—C(R$_1$)(R$_2$)—O—C(O)—X, wherein:

Ar is an optionally substituted fused polycyclic aryl or heteroaromatic group or a vinylogous derivative thereof, R$_1$ and R$_2$ are independently H, optionally substituted alkyl, alkenyl or alkynyl, optionally substituted aryl or optionally substituted heteroaromatic, or a vinylogous derivative of the foregoing; and X is a leaving group, a chemical fragment linked to Ar—C(R$_1$)(R$_2$)—O—C(O)— via a heteroatom, or a solid support; provided that when Ar is 1-pyrenyl and R$_1$=R$_2$=H, X is not linked to Ar—C(R$_1$)(R$_2$)—O—C(O)— via a nitrogen atom.

Preferred embodiments are those in which Ar is a fused polycyclic aromatic hydrocarbon and in which the substituents on Ar, R$_1$ and R$_2$ are electron donating groups, such as alkoxy groups, particularly one or more methoxy groups. Examples of electron donating carrying R$_1$ and R$_2$ groups are methyl, substituted phenyl groups, e.g., o- or p-methoxyphenyl; 2,6-dimethoxyphenyl; 2,3-dimethoxyphenyl; 3,5-dimethoxyphenyl and the like. Other R$_1$ and R$_2$ groups include 9-anthracenyl or 1-pyrenyl. Particularly preferred protecting groups are the "PYMOC" protecting group, 1-pyrenylmethyloxycarbonyl, where Ar=1-pyrenyl and R$_1$=R$_2$=H, and the "ANMOC" protecting group, anthracenylmethyloxycarbonyl, where Ar=anthracenyl (e.g. 9-anthracenyl) and R$_1$=R$_2$=H.

Representative fused polycyclic aromatic hydrocarbons include naphthalene, phenanthrene, anthracene, benzoanthracene, dibenzoanthracene, heptalene, acenaphthalene, acephenanthrene, triphenylene, pyrene, fluorene, phenalene, naphthacene, picene, perylene, pentaphenylene, pyranthrene, fullerenes (including C$_{60}$ and C$_{70}$), and the like. A representative vinylogously substituted derivative of an aromatic hydrocarbon is styrene.

The invention also provides reagents of the molecular formula Ar—C(R$_1$)(R$_2$)—O—C(O)—X, where Ar, R$_1$, and R$_2$ have the meanings ascribed above, for incorporating the protecting group into the molecule desired to be protected. X can be any suitable leaving group such as halo, oxycarbonyl, imidazolyl, pentafluorophenoxy and the like, which is capable of reacting with a nucleophilic group such as hydroxy, amino, alkylamino, thio and the like on the molecule being protected. Thus, the reagents comprising the protecting groups Ar—C(R$_1$)(R$_2$)—O—C(O)— disclosed herein can be used in numerous applications where protection of a reactive nucleophilic group is required. Such applications include, but are not limited to polypeptide synthesis, both solid phase and solution phase, oligo- and polysaccharide synthesis, polynucleotide synthesis, protection of nucleophilic groups in organic syntheses of potential drugs, etc.

The invention also provides compositions of the molecular formula Ar—C(R$_1$)(R$_2$)—O—C(O)—M, where Ar, R$_1$ and R$_2$ have the meaning outlined above and M is any other chemical fragment. Preferably, M will be a monomeric building block that can be used to make a macromolecule. Such building blocks include amino acids, peptides, polypeptides, nucleic acids, nucleotides, nucleosides, monosaccharides, and the like. Preferred nucleosides are ribonucleosides and deoxyribonucleosides such as adenosine, deoxyadenosine, cytidine, deoxycytidine, thymidine, uracil, guanosine and deoxyguanosine as well as oligonucleotides incorporating such nucleosides. Preferably, the building block is linked to the photolabile protecting group via a hydroxy or amine group. When nucleotide and oligonucleotide compositions are used, with the protecting groups of this invention, the protecting groups are preferably incorporated into the 3'-OH or the 5'-OH of the nucleoside. Other preferred compounds are protected peptides, proteins, oligonucleotides and oligodeoxyribonucleotides. Small organic molecules, proteins, hormones, antibodies and other such species having nucleophilic reactive groups can be protected using the protecting groups disclosed herein.

The use of nucleoside and nucleotide analogs is also contemplated by this invention to provide oligonucleotide or oligonucleoside analogs bearing the protecting groups disclosed herein. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into an oligonucleotide or oligonucleoside sequence, they allow hybridization with a naturally occurring oligonucleotide sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Analogs also include protected and/or modified monomers as are conventionally used in oligonucleotide synthesis. As one of skill in the art is well aware oligonucleotide synthesis uses a variety of base-protected deoxynucleoside derivatives in which one or more of the nitrogens of the purine and pyrimidine moiety are protected by groups such as dimethoxytrityl, benzyl, tert-butyl, isobutyl and the like. Specific monomeric building blocks which are encompassed by this invention include base protected deoxynucleoside H-phosphonates and deoxynucleoside phosphoramidites.

For instance, structural groups are optionally added to the ribose or base of a nucleoside for incorporation into an oligonucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary nucleic acids (especially RNA) than their unmodified counterparts. 2'-O-MeORNA phosphoramidite monomers are available commercially, e.g., from Chem Genes Corp. or Glen Research, Inc. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the oligonucleotide analogue can also be substituted or modified, for instance with methyl phosphonates or O-methyl phosphates. Another example of an oligonucleotide analogue for purposes of this disclosure includes "peptide nucleic acids" in which a polyamide backbone is attached to oligonucleotide bases, or modified oligonucleotide bases. Peptide nucleic acids which comprise a polyamide backbone and the bases found in naturally occurring nucleosides are commercially available from, e.g., Biosearch, Inc. (Bedford, Mass.).

Nucleotides with modified bases can also be used in this invention. Some examples of base modifications include 2-aminoadenine, 5-methylcytosine, 5-(propyn-1-yl) cytosine, 5-(propyn-1-yl)uracil, 5-bromouracil, and 5-bromocytosine which can be incorporated into oligonucleotides in order to increase binding affinity for complementary nucleic acids. Groups can also be linked to various positions on the nucleoside sugar ring or on the purine or pyrimidine rings which may stabilize the duplex by electrostatic interactions with the negatively charged phosphate backbone, or through hydrogen bonding interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified oligonucleotides and oligonucleotide analogs suitable for use in this invention are described in, e.g., "Antisense Research and Applications", S. T. Crooke and B. LeBleu (eds.) (CRC Press, 1993) and "Carbohydrate Modifications in Antisense Research" in ACS Symp. Ser. #580, Y. S. Sanghvi and P. D. Cook (eds.) ACS, Washington, D.C. 1994).

Compounds of this invention can be prepared by carbonylating an aromatic carbinol of the general formula Ar—C($R_1$)($R_2$)—OH with a carbonylation reagent such as for example, phosgene ($COCl_2$), carbonyldiimidazole or pentafluorophenoxy chloroformate and the like to provide Ar—C($R_1$)($R_2$)—O—C(O)—X where X is a leaving group derived from the carbonylating reagent (Cl, if phosgene was used, pentafluorophenoxy, if pentafluorophenoxy chloroformate was used, etc.). This intermediate, Ar—C($R_1$)($R_2$)—O—C(O)—X is then reacted with a molecule M carrying a nucleophilic group whose protection is desired to yield a protected building block Ar—C($R_1$)($R_2$)—O—C(O)-M. Representative aromatic carbinols are pyrenemethanol, naphthalenemethanol, anthracenemethanol, perylenemethanol and the like. Such aromatic carbinols are available from commercial suppliers such as Aldrich Chemical Co., Milwuakee, Wis. Alternatively, they may also be obtained from precursor aromatic hydrocarbons by acylation under Friedel-Crafts conditions with acid chlorides and anhydrides and subsequent reduction of the carbonyl group thus added to a carbinol.

Alternatively, one may first carbonylate the group on the molecule being protected with a carbonylation reagent, such as one described above, and subsequently displace the leaving group X thus inserted with the hydroxyl group of the aromatic carbinol. In either procedure, one frequently uses a base such as triethylamine or diisopropylethylamine and the like to facilitate the displacement of the leaving group.

One of skill in the art will recognize that the protecting groups disclosed herein can also be attached to species not traditionally considered as "molecules". Therefore, compositions such as solid surfaces (e.g., paper, nitrocellulose, glass, polystyrene, silicon, modified silicon, GaAs, silica and the like), gels (e.g., agarose, sepharose, polyacrylamide and the like) to which the protecting groups disclosed herein are attached are also contemplated by this invention.

The protecting groups of this invention are typically removed by photolysis, i.e., by irradiation, though in selected cases it may be advantageous to use acid or base catalyzed cleavage conditions. Generally irradiation is at wavelengths greater than about 340 nm, preferably at about 365 nm. The photolysis is usually conducted in the presence of hydroxylic or protic solvents, such as aqueous, alcoholic or mixed aqueous-alcoholic or mixed aqueous-organic solvent mixtures. Alcoholic solvents frequently used include methanol and ethanol. The photolysis medium may also include nucleophilic scavengers such as hydrogen peroxide. Photolysis is frequently conducted at neutral or basic pH.

This invention also provides a method of attaching a molecule with a reactive site to a support, comprising the steps of:

(a) providing a support with a reactive site;

(b) binding a molecule to the reactive site, said first molecule comprising a masked reactive site attached to a photolabile protecting group of the formula Ar—C($R_1$) ($R_2$)—O—C(O)—, wherein:

Ar is an optionally substituted fused polycyclic aryl or heteroaromatic group or a vinylogously substituted derivative of the foregoing;

$R_1$ and $R_2$ are independently H, optionally substituted alkyl, alkenyl or alkynyl, or optionally substituted aryl or heteroaromatic group or a vinylogously substituted derivative of the foregoing;

to produce a derivatized support having immobilized thereon the molecule attached to the photolabile protecting group; and (c) removing the photolabile protecting group to provide a derivatized support comprising the molecule with an unmasked reactive site immobilized thereon.

As one of skill will recognize, the process can be repeated to generate a compound comprising a chain of component molecules attached to the solid support. In a "mix and match" approach, the photolabile protecting groups may be varied at different steps in the process depending on the ease of synthesis of the protected precursor molecule. Alternatively, photolabile protecting groups can be used in some steps of the synthesis and chemically labile (e.g. acid or base sensitive groups) can be used in other steps, depending for example on the availability of the component monomers, the sensitivity of the substrate and the like. This method can also be generalized to be used in preparing arrays of compounds, each compound being attached to a different and identifiable site on the support as is disclosed in U.S. Pat. Nos. 5,143,854, 5,384,261, 5,424,186 5,445,934 and copending U.S. patent application Ser. No. 08/376,963, filed Jan. 23, 1995, incorporated herein by reference for all purposes.

Thus, a related aspect of this invention provides a method of forming, from component molecules, a plurality of compounds on a support, each compound occupying a separate predefined region of the support, said method comprising the steps of:

(a) activating a region of the support;

(b) binding a molecule to the region, said molecule comprising a masked reactive site linked to a photolabile protecting group of the formula Ar—C($R_1$)($R_2$)—O—C (O)—, wherein:

Ar is an optionally substituted fused polycyclic aryl or heteroaromatic group or a vinylogously substituted derivative of the foregoing;

$R_1$ and $R_2$ are independently H, optionally substituted alkyl, alkenyl or alkynyl, or optionally substituted aryl or heteroaromatic group or a vinylogously substituted derivative of the foregoing;

(c) repeating steps (a) and (b) on other regions of the support whereby each of said other regions has bound thereto another molecule comprising a masked reactive site linked to the photolabile protecting group, wherein said another molecule may be the same or different from that used in step (b);

(d) removing the photolabile protecting group from one of the molecules bound to one of the regions of the support to provide a region bearing a molecule with an unmasked reactive site;

(e) binding an additional molecule to the molecule with an unmasked reactive site;

(f) repeating steps (d) and (e) on regions of the support until a desired plurality of compounds is formed from the component molecules, each compound occupying separate regions of the support.

A related method of forming a plurality of compounds on predefined regions of a support involves binding a molecule with a reactive site protected with a chemically labile protecting group to an activated region of the support and chemically removing the chemically labile protecting group to reveal the reactive site. The reactive site is then protected with a photolabile protecting group of this invention. This process is repeated for other regions of the support with other molecules as desired to provide a support having molecules with reactive sites protected by photolabile protecting groups on separate regions of the support. Reactive sites can be unmasked by removing the photolabile group from selected regions and coupled to additional molecules with photolabile protecting groups as described earlier to build up arrays of compounds on the support. Again, in a "mix and match" approach, monomers with chemically labile protecting groups can be attached to a reactive site on the substrate (i.e., on the support itself when the first layer of monomers is being assembled or subsequently onto an already attached monomer whose reactive site has been unmasked) and these chemically labile protecting groups can be replaced by a photolabile protecting groups of this invention. The replacement is accomplished by removing the chemically labile protecting group under conditions which do not affect any photolabile groups which may be on the support. This then reveals an unmasked reactive site on the monomer which had carried the chemically labile protecting group and this unmasked reactive site is reacted with a reagent of the formula Ar—C($R_1$)($R_2$)—O—C(O)—X, where X is a leaving group. Thereby, this region of the support is protected by a photolabile protecting group which can be selectively removed by light directed systems described in U.S. Pat. Nos. 5,143,854, 5,384,261, 5,424,186 and 5,445,934 and further described below. This method is particularly useful when the monomers are more readily available carrying chemically labile protecting groups than the photolabile protecting groups described herein. It will be recognized that any method of forming a chain of compounds or an array of compounds on a support using in at least one step a protecting group/reagent or compound of this invention is within the scope of the methods this invention.

Generally, these methods involve sequential addition of monomers to build up an array of polymeric species on a support by activating predefined regions of a substrate or solid support and then contacting the substrate with a protected monomer of this invention (e.g., a PYMOC protected nucleoside or amino acid). It will be recognized that the individual monomers can be varied from step to step. A common support is a glass or silica substrate as is used in semiconductor devices.

The predefined regions can be activated with a light source, typically shown through a screen such as a photolithographic mask similar to the techniques used in integrated circuit fabrication. Other regions of the support remain inactive because they are blocked by the mask from illumination and remain chemically protected. Thus, a light pattern defines which regions of the support react with a given monomer. The protected monomer reacts with the activated regions and is immobilized therein. The protecting group is removed by photolysis and washed off with unreacted monomer. By repeatedly activating different sets of predefined regions and contacting different monomer solutions with the substrate, a diverse array of polymers of known composition at defined regions of the substrate can be prepared. Arrays of $10^6$, $10^7$, $10^8$, $10^9$, $10^{10}$, $10^{11}$, $10^{12}$ or more different polymers can be assembled on the substrate. The regions may be 1 mm$^2$ or larger, typically 10 $\mu$m$^2$ and may be as small as 1 $\mu$m$^2$. These regions are also referred to herein as "features."

In the preferred methods of preparing these arrays, contrast between features may be enhanced through the front side exposure of the substrate. By "front side exposure" is meant that the activation light is incident upon the synthesis side of the substrate, contacting the synthesis side of the substrate prior to passing through the substrate. Front side exposure reduces effects of diffraction or divergence by allowing the mask to be placed closer to the synthesis surface. Additionally, and perhaps more importantly, refractive effects from the light passing through the substrate surface, prior to exposure of the synthesis surface, are also reduced or eliminated by front-side exposure. Front side exposure is described in substantial detail in U.S. patent application Ser. No. 08/634,053 filed Apr. 17, 1996, incorprated herein by reference.

As noted previously, however, the efficiency of photolysis of the preferred photolabile protecting groups of the present invention is improved when such photolysis is carried out in the presence of nucleophilic solvents, such as water or methanol. This presents a unique problem where front side photolysis is used. Specifically, as the front side of the substrate is exposed to the activation radiation, a flow cell cannot be used to maintain the desired nucleophilic environment during such photolysis. Accordingly, in preferred aspects, light-directed synthesis methods employing the protecting groups of the present invention is carried out by providing a thin aqueous film or coating on the synthesis surface of the substrate. The presence of this thin film or coating allows one to control the local environment on the synthesis surface, i.e., to provide conditions that are favorable for that synthesis. By "conditions favorable to reaction" is meant conditions that result in an improvement of reaction efficiency of a given chemical reactant or reactants, over reactions not performed in that environment, e.g., reaction rate, yield, or both. For example, for synthesis methods employing the protecting groups described herein, coatings may be applied that provide a nucleophic environment which is favorable to photolysis of the protecting group, and which thereby promotes efficient synthesis. The use of such coatings also permits the front side exposure of the substrate surface. This method may also be performed in reacting more than one chemical reactant, by applying both reactants on the surface prior to coating, or by adding the second reactant after the coating or as an element of the coating.

Generally, a thin film or coating of aqueous solution can be applied to the synthesis surface of a substrate that is bearing the protecting groups of the invention, e.g., that has been subjected to previous synthesis steps. Application of the coating may be carried out by methods that are well known in the art. For example, spin-coating methods may be utilized where the substrate is spun during application of the coating material to generate a uniform coating across the surface of the substrate. Alternative application methods may also be used, including simple immersion, spray coating methods and the like.

Aqueous solutions for use as coating materials typically include, e.g., low molecular weight poly-alcohols, such as ethylene glycol, propylene glycol, glycerol and the like. These solutions are generally hygrophilic and provide nucleophilic hydroxyl groups which will also support the photolysis reaction. The poly-alcohols also increase the viscosity of the solution, which can be used to control the thickness of the coating. Higher molecular weight poly-alcohols, i.e., polyvinyl alcohol, may also be used to adjust the viscosity of the coating material.

Generally, preferred substrates have relatively hydrophobic surfaces. As such, the aqueous coating solution may also include an appropriate surfactant, e.g., from about 0.01 to about 10% v/v to permit spreading and adhesion of the film upon the substrate surface. Such surfactants generally include those that are well known in the art, including, e.g., Triton X-100, Tween-80, and the like. In addition to promoting the spreading and adhesion of the coating to the substrate, addition of a these non-volatile solutes within the coating solution can limit the amount of evaporation of the film and promote its longevity.

The methods described herein may also employ component molecules comprising a masked reactive site attached to a photolabile protecting group of the formula Ar—C($R_1$)($R_2$)—, wherein Ar, $R_1$, and $R_2$ have the meanings ascribed earlier. In such cases, the protecting group is attached to a reactive site that is not an amine and is removed by photolysis.

The solid substrate or solid support may be of any shape, although they preferably will be roughly spherical. The supports need not necessarily be homogenous in size, shape or composition, although the supports usually and preferably will be uniform. In some embodiments, supports that are very uniform in size may be particularly preferred. In another embodiment, two or more distinctly different populations of solid supports may be used for certain purposes.

Solid supports may consist of many materials, limited primarily by capacity for derivatization to attach any of a number of chemically reactive groups and compatibility with the synthetic chemistry used to produce the array and, in some embodiments, the methods used for tag attachment and/or synthesis. Suitable support materials typically will be the type of material commonly used in peptide and polymer synthesis and include glass, latex, polyethylene glycol, heavily cross-linked polystyrene or similar polymers, gold or other colloidal metal particles, and other materials known to those skilled in the art. The chemically reactive groups with which such solid supports may be derivatized are those commonly used for solid phase synthesis of the polymer and thus will be well known to those skilled in the art, i.e., carboxyls, amines, and hydroxyls.

To improve washing efficiencies, one can employ nonporous supports or other solid supports less porous than typical peptide synthesis supports; however, for certain applications of the invention, quite porous beads, resins, or other supports work well and are often preferable. One such support is a resin in the form of beads. In general, the bead size is in the range of 1 nm to 100 $\mu$m, but a more massive solid support of up to 1 mm in size may sometimes be used. Particularly preferred resins include Sasrin resin (a polystyrene resin available from Bachem Bioscience, Switzerland); and TentaGel S AC, TentaGel PHB, or TentaGel S NH$_2$ resin (polystyrene-polyethylene glycol copolymer resins available from Rappe Polymere, Tubingen, Germany). Other preferred supports are commercially available from and described by Novabiochem, La Jolla, Calif.

In other embodiments, the solid substrate is flat, or alternatively, may take on alternative surface configurations. For example, the solid substrate may contain raised or depressed regions on which synthesis takes place. In some embodiments, the solid substrate will be chosen to provide appropriate light-absorbing characteristics. For example, the substrate may be a polymerized Langmuir Blodgett film, functionalized glass, Si, Ge, GaAs, GaP, SiO$_2$, SiN$_4$, modified silicon, or any one of a variety of gels or polymers such as (poly)tetrafluorethylene, (poly)vinylidendifluoride, polystyrene, polycarbonate, or combinations thereof. Other suitable solid substrate material will be readily apparent to those of skill in the art. Preferably, the surface of the solid substrate will contain reactive groups, which could be carboxyl, amino, hydroxyl, thiol, or the like. More preferably, the surface will be optically transparent and will have surface Si—OH functionalities, such as are found on silica surfaces.

The photolabile protecting groups and protected monomers disclosed herein can also be used in bead based methods of immobilization of arrays of molecules on solid supports.

A general approach for bead based synthesis is described in copending application Ser. No. 07/762,522 (filed Sep. 18, 1991); Ser. No. 07/946,239 (filed Sep. 16, 1992); Ser. No. 08/146,886 (filed Nov. 2, 1993); Ser. No. 07/876,792 (filed Apr. 29, 1992) and PCT/US93/04145 (filed Apr. 28, 1993), Lam et al. (1991) Nature 354:82–84; PCT application no. 92/00091 and Houghten et al, (1991) Nature 354:84–86, each of which is incorporated herein by reference for all purposes.

Other methods of immobilization of arrays of molecules in which the photocleavable protecting groups of this invention can be used include pin based arrays and flow channel and spotting methods.

Photocleavable arrays also can be prepared using the pin approach developed by Geysen et al. for combinatorial solid-phase peptide synthesis. A description of this method is offered by Geysen et al., J. Immunol. Meth. (1987) 102:259–274, incorporated herein by reference.

Additional methods applicable to library synthesis on a single substrate are described in co-pending application Ser. No. 07/980,523, filed Nov. 20, 1992, and Ser. No. 07/796,243, filed Nov. 22, 1991, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites. Photocleavable linkers are particularly suitable for this technology as this delivery method may otherwise result in poor synthesis fidelity due to spreading, reagent dilution, inaccurate delivery, and the like. By using a photocleavable linker, rather than a conventional acid-cleavable linker, the purest material can be selectively cleaved from the surface for subsequent assaying or other procedures. More specifically, masks can be used when cleaving the linker to ensure that only linker in the center of the delivery area (i.e., the area where reagent delivery is most consistent and reproducible) is cleaved. Accordingly, the material thus selectively cleaved will be of higher purity than if the material were taken from the entire surface.

Typically, the molecules used in this method will be the monomeric components of complex macromolecules. These monomeric components can be small ligand molecules, amino acids, nucleic acids, nucleotides, nucleosides, monosaccharides and the like, thereby allowing one to synthesize arrays of complex macromolecules or polymeric sequences, such as polypeptides, nucleic acids and synthetic receptors, on the solid support.

This invention discloses new nucleoside phosphoramidite monomers with 1-pyrenylmethyloxy-carbonyl ("PYMOC") 5'-protecting groups. They are photolytically cleaved under irradiation at wavelengths greater than about 340 nm, preferably at about 365 nm, in the presence of methanol, water, or water-solvent mixtures and/or with nucleophilic scavengers such as hydrogen peroxide at neutral or basic pH. The rate of photolysis is similar to that observed for the MeNPOC group. However, the yield of PYMOC photo-removal is much higher (~95%), so that the use of these monomers for photochemical synthesis of oligonucleotides leads to higher stepwise cycle yields and therefore higher-purity oligomers.

The 1-pyrenylmethyloxycarbonyl group described here can be used for the protection of alcohols. The photolysis of PYMOC is faster than that of the 1-pyrenylmethyl group, so it would also be a superior photo-removable protecting group for phosphates, carboxylates, amines, thiols, etc.

Figure 2:
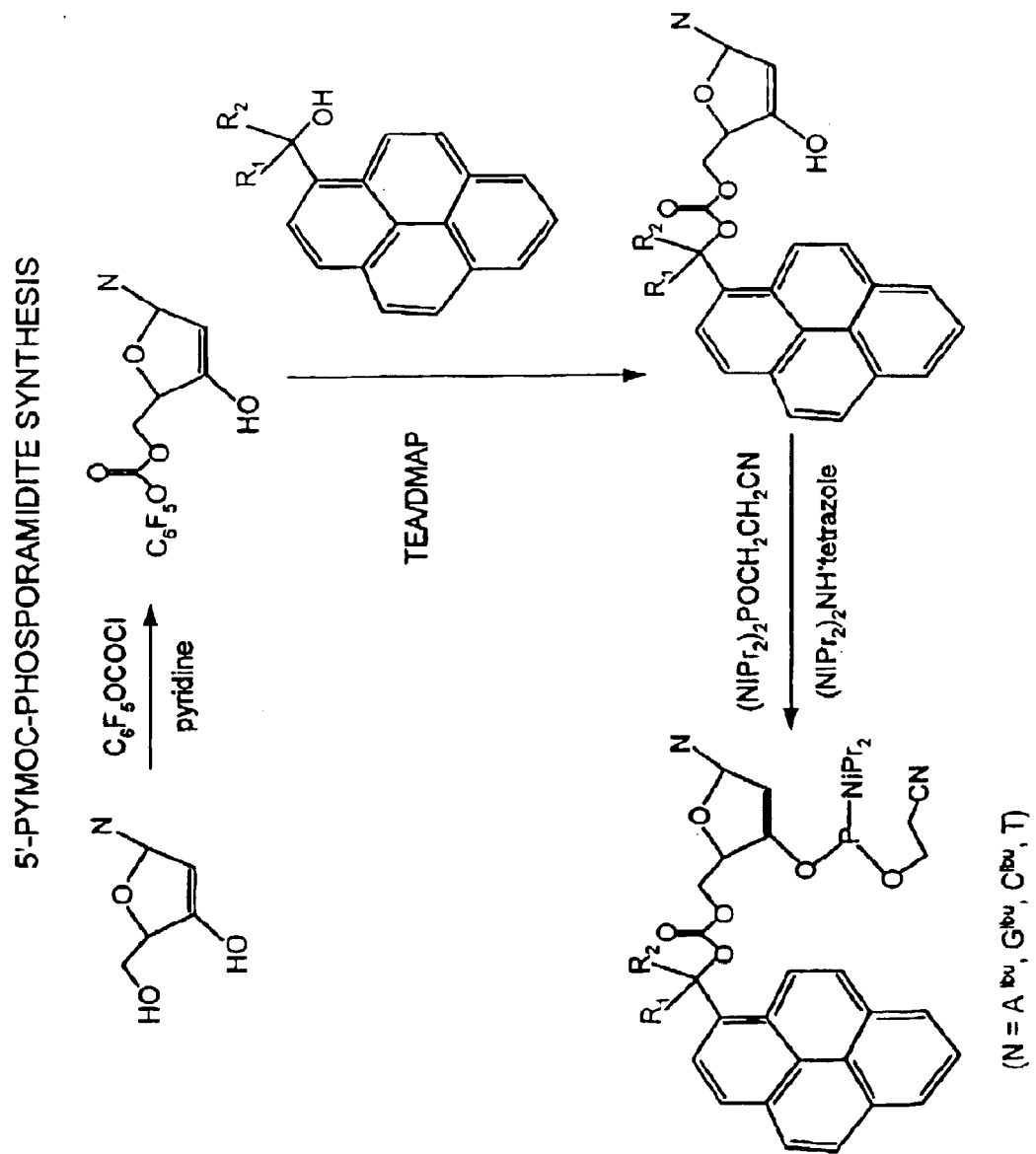
Figure 3:
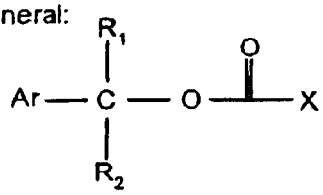
FIG. 3 shows representative Ar groups that can be present in the compounds of this invention.
Figure 3:
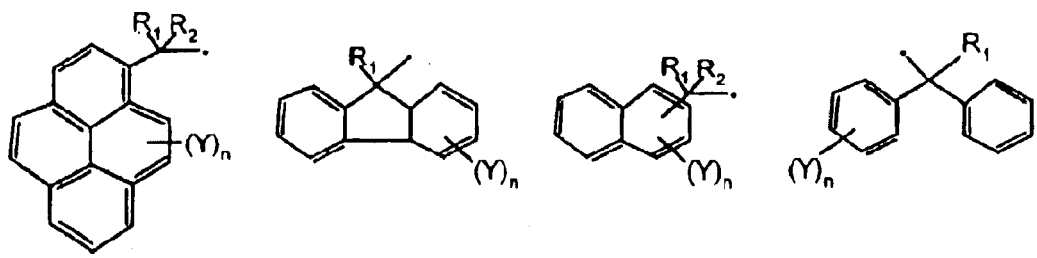
Figure 3:
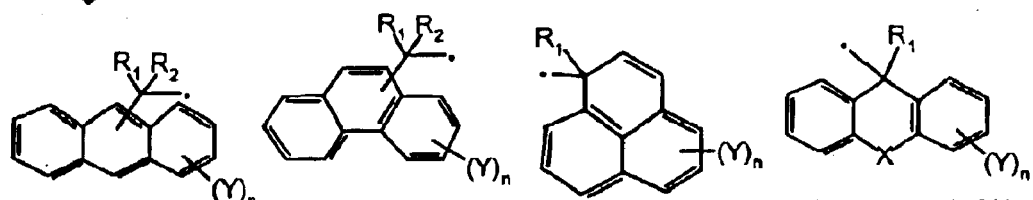
Figure 3:
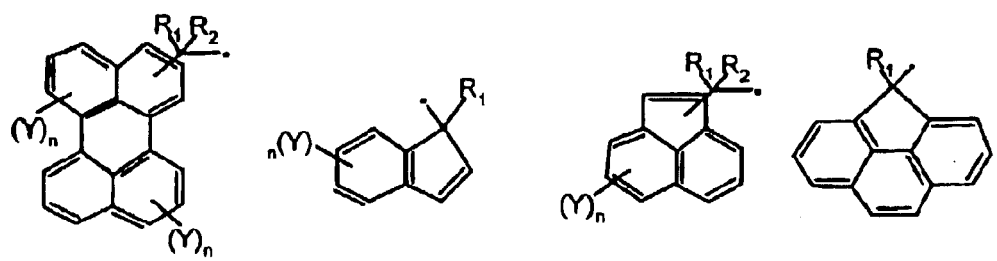
Figure 3:
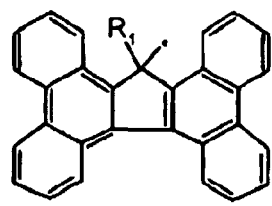

Other "benzylic" oxycarbonyls may have similar or better efficiency than the PYMOC group. A general formula would be:

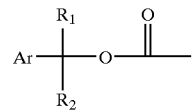

where Ar is an optionally substituted fused polycyclic aryl or an optionally substituted heteroaromatic group or a vinylogously substituted derivative of the foregoing;

R$_1$ and R$_2$ are independently H, optionally substituted alkyl, alkenyl or alkynyl, optionally substituted aryl, optionally substituted heteroaromatic, or vinylogously substituted derivatives of the foregoing. Preferred embodiments are those in which Ar is a fused polycyclic aromatic hydrocarbon. FIG. 2 shows representative examples. Preferred substituents on the aromatic hydrocarbons would be electron-donating groups that stabilize an incipient excited state benzyl carbocation.

Other embodiments of the PYMOC photogroup, for example, include at least one additional substituent at the a position, such as a methyl group or a methoxy-substituted phenyl. These substituents will increase photosolvolysis efficiency, and improve the selectivity for the 5'-hydroxyl in the preparation of the monomer 5'-protected nucleoside.

EXAMPLES

Synthesis of 5'-O-PYMOC-2'-DEOXYNUCLEOSIDE-3'-O-(N,N-DIISOPROPYL) CYANOETHYLPHOSPHORAMIDITES All chemical reagents used were procured from commercial sources (Aldrich Chemical Co., Milwaukee, Wis. and Sigma Chemical Co., Milawaukee, Wis.). Intermediates and products were identified by mass spectrometry, $^1$H-NMR, and $^{31}$P-NMR.

Abbreviations:
DIEA—Diethyl isopropylamine
NHS—N-hydroxysuccinimide
THF—Tetrahydrofuran
MeNPOC—methylnitropiperonyloxycarbonyl
TEA—Triethylamine
DMAP—4-Dimethylaminopyridine
Pentafluorophenyl Chloroformate Pentafluorophenol (30 g; 163 mmol) and triethylamine (20 g, 200 mmol) were combined in 200 ml dry THF, and then added dropwise to a stirring solution of phosgene (20 g; 200 mmol) in 100 ml of toluene at 0° C. After 2 hours, the solution was filtered and evaporated to give the crude product as an oil, which was recrystallized from hexane to obtain 30 g (75%) pure pentafluorophenyl chloroformate.

5'-O-(1-Pyrenylmethyl)- and 5'-O-(9-anthracenylmethyl)oxycarbonyl-2'-deoxynucleosides The following general procedure was used to prepare 5'-PYMOC-derivatives of thymidine, N-4-isobutyryl-2'-deoxycytidine, N-7-isobutyryl-2'-deoxyadenosine, and N-4-isobutyryl-2'-deoxyguanosine; and 5'-ANMOC isobutyryl-2'-deoxyadenosine:

The base-protected nucleoside (20 mmol) was dried by co-evaporating 3 times with 50 ml dry pyridine, then dissolved in 20 ml $CH_2Cl_2$ and 10 ml dimethylsulfoxide (DMSO) containing 1.7 ml (21 mmol) pyridine. The resulting solution was cooled to −10° C. under argon, and 5 g (20 mmol) of pentafluorophenyl chloroformate was added all at once with stirring. After an additional 2–3 hours stirring at −110° C., the reaction mixture was analyzed by TLC or HPLC to determine the extent of conversion. Additional quantities of pentafluorophenyl chloroformate and pyridine (~0.4–1.0 mmol each) were then added, as needed, until the nucleoside was completely converted to the 5'-O-pentafluorophenoxycarbonyl derivative. Although isolable, at this point the intermediate was usually converted directly to the PYMOC or ANMOC-derivative, in situ, by the addition of 1-pyrenemethanol (6 g, 26 mmol) or 9-anthracenemethanol, followed by 10 ml of triethylamine and 0.25 g (2 mmol) of N,N-dimethyl-aminopyridine, and stirring overnight at room temperature. About 50–100 ml of $CH_2Cl_2$ was then added, and in the case of thymidine, the pure PYMOC-derivative precipitated and could be collected by filtration. Otherwise, the solution was washed twice with 5% aqueous $NaHCO_3$, once with saturated NaCl, dried with $Na_2SO_4$, and evaporated to dryness. The crude material was finally purified by flash chromatography (silica gel, 2:8 ethyl acetate-$CH_2Cl_2$/1–6% methanol gradient) to obtain the pure 5'-PYMOC or ANMOC nucleoside products in ~75% yield. The purity of the nucleosides was determined by HPLC, $^1$H-NMR, mass spectrometry and elemental analysis (CHN).

5'-O-(1-Pyrenylmethyl)oxycarbonyl-2'-deoxynucleoside-3'-O—(N,N-diisopropyl)Cyanoethylphosphoramidites On a 12 mmol scale, the 5'-PYMOC and ANMOC nucleosides were first dried by co-evaporation with dry pyridine, and then dissolved or suspended in 50 ml of dry $CH_2Cl_2$. Then 2-cyanoethyl-N,N,$N^1$,$N^1$-tetraisopropylphosphorodiamidite (4.4 g; 14.5 mmol) and N,N-diisopropylammonium tetrazolide (1 g; 6 mmol) were added, and the mixture was left stirring under argon overnight. The solution was washed twice with 10% aqueous $NaHCO_3$, once with saturated NaCl, dried with $Na_2SO_4$, and then evaporated to dryness. The crude products were purified by flash chromatography (silica gel, eluting with a 1–5% methanol gradient in 2:8 ethyl acetate-$CH_2Cl_2$ containing 0.5% triethylamine) to obtain the pure phosphoramidites in ~80% yield. Purity was established by HPLC, $^1$H, $^{31}$P-NMR, mass spectrometry and elemental analysis (CHN)

Table 1 compares the efficiency of photolytic cleavage of PYMOC and ANMOC protected nucleosides to MeNPOC (methylnitropiperonyloxycarbonyl) protected nucleosides.

TABLE 1

Photolysis Rates:

| Base | 5'-Protecting Group | Solvent | Power | $T_{1/2}$ |
|---|---|---|---|---|
| T | MeNPOC | dioxane | 35 mW/cm$^2$ | 9 sec |
| T | PYMOC | MeOH | " | 10 sec |
| T | PYMOC | 1:1 dioxane-$H_2O$ | " | 10 sec |
| T | PYMOC | 9:1 dioxane-MeOH | " | 43 sec |
| G$^{ibu}$ | MeNPOC | dioxane | 27 mW/cm$^2$ | 11 sec |
| G$^{ibu}$ | PYMOC | MeOH | " | 13 sec |
| C$^{ibu}$ | MeNPOC | dioxane | " | 12 sec |
| C$^{ibu}$ | PYMOC | MeOH | " | 27 sec |
| A$^{ibu}$ | MeNPOC | dioxane | " | 12 sec |
| A$^{ibu}$ | PYMOC | MeOH | " | 12 sec |
| A$^{ibu}$ | ANMOC | MeOH | " | 17 sec |

Table 2 compares the coupling cycle efficiency (six cycles) of PYMOC protected and MeNPOC protected nucleosides to a hydroxyalkylsilanated glass support using surface fluorescence analysis.

TABLE 2

Stepwise Coupling Cycle Efficiencies:
1. Surface fluorescence analysis ("staircase" assay):

| | 5'-Protecting | Yield (6 steps) | |
| Base | Group | Net | Avg. Stepwise |
|---|---|---|---|
| T | MeNPOC | 15 | 73 |
| T | PYMOC | 56 | 91 |
| dG$^{ibu}$ | MeNPOC | 29 | 81 |
| dG$^{ibu}$ | PYMOC | 61 | 92 |
| dC$^{ibu}$ | MeNPOC | 37 | 85 |
| dC$^{ibu}$ | PYMOC | 68 | 94 |
| dA$^{pac}$ | MeNPOC | 40 | 86 |
| dA$^{ibu}$ | PYMOC | 73 | 95 |
| dA$^{ibu}$ | ANMOC | 68 | 94 |

Table 3 compares the coupling cycle efficiency (six cycles) of PYMOC protected and MeNPOC protected nucleosides to a solid support using HPLC analysis.

TABLE 3

2. HPLC analysis (DOP#AF001; 3" ethenodeoxyadenosine tag):

| | 5'-Protecting | Yield (3 steps) | |
| Base | Group | Net | Avg. Stepwise |
|---|---|---|---|
| T | PYMOC | 92 | 97.2 |
| T | " | 93 | 97.6 avg 97.4 |
| T | MeNPOC | 45 | 77 |
| T | " | 43 | 75 |
| T | " | 48 | 78 |
| T | " | 40 | 74 |
| T | " | 48 | 78 avg 76.4 |

Front Side Photolysis Using PYMOC Protecting Groups

Two experiments were conducted using HO-PEG modified substrates on which 5'-PYMOC thymidine amidite had been covalently coupled in a previous synthesis step. Striped regions of the surface were exposed at 365 nm at 35 mW/cm$^2$ for 200 seconds, under each of the following conditions: (1) dry or uncoated; (2) coated; and (3) wet (in a flow cell with Water/MeOH).

For the coated exposures, two coatings were tested: (1) 1% Triton X-100 in $H_2O$; and (2) 0.2% Triton X-100 in 50% glycerol/H$_2$O. The coating was rinsed off the substrate with dry acetonitrile in a flowcell, after the exposure. The substrates were then stained with Fluoreprime™ amidite (Pharmacia), and scanned on a confocal laser scanner. The relative extent of photolysis for each exposure was determined from the fluorescent intensities of each stripe. The results shown in FIG. 4 show that both coated films greatly enhanced photolysis over the dry exposure. FIG. 4, panel A shows the fluorescent scans of uncoated or dry photolysis (left stripe), coated photolysis using 1% Triton X-100 in H$_2$O (center stripe) and wet photolysis conducted in a flow cell with Methanol/H$_2$O (right stripe). Panel B shows uncoated or dry photolysis (left stripe), coated photolysis using 0.2% Triton X-100 in 50% glycerol/H$_2$O (center stripe), and wet photolysis as described above (right stripe).

The Triton-water coating showed the best performance at 95% of the intensity of the wet exposure (normalized at 100%), whereas the Triton/glycerol/water coating yielded 71% of the fluorescent intensity. The two dry exposures yielded 23% and 35% of the wet exposure intensity.

Hybridization Characteristics of DNA Probe Arrays Made with 5'-PYMOC Phosphoramidites A test array comprised of 256 decanucleotides, defined by the sequence 5'-TNCNGTNCAN-3'(SEQ ID NO:1), where N=A, C, G or T, was synthesized on an Affymetrix Array Synthesizer using 5'-PYMOC-dAiBu, dGiBu, dCiBu & T phosphoramidites. The coupling and masking procedures used to prepare the array were the same as those described elsewhere (Pease, A. C., et al. (1994) Proc. Natl. Acad. Sci. USA 91, 5022–5026), except that the photolysis step in each cycle was carried with methanol in contact with the surface of the substrate. For comparison, the same array was also synthesized by the previously described process using 5'-O-(a-methyl-6-nitropiperonyloxycarbonyl-"MeNPOC")-nucleoside monomers (photolysis in dioxane). The array was made on a glass slide which had been silanated with N,N-bis(hydroxyethyl) aminopropyltriethoxysilane as described previously (Pease, A. C., et al., (1994)), and then adding to the surface a photolysable linker, MeNPOC-hexaethyleneglycol-(2-cyanoethyl-N,N-diisopropyl) phosphoramidite. Since oligonucleotide synthesis is more efficient with the PYMOC-building blocks, the density of "active" synthesis sites on the substrate was reduced prior to synthesis in order to make a better comparison with the less efficient array synthesis of the MeNPOC building blocks. This was achieved by photo-deprotecting 90–95% of the surface MeNPOC groups by partial photolysis (i.e., exposure to light for four half-lives), and then capping the free hydroxyl groups with a mixture of tetrazole and diethoxy-N,N-diisopropylaminophosphine. After deprotecting the array in 50% ethanolic ethylenediamine for 6 hours, hybridization of a complementary fluoresein-labelled oligonucleotide "target" (5'-fluorescein-ACTGGACTGAACGGTAATGCAC-3'(SEQ ID NO:2)) was carried out at 5 nM concentration in 5×-SSPE buffer (pH 7.4), in a flowcell fixed to the stage of a scanning fluorescence microscope. Hybridization to the array was determined by scanning the surface of the substrate to acquire a surface fluorescence image. The hybridization images that were obtained are shown in FIGS. 5a and 5b. The congruence of these images, demonstrates that the array fabricated with the PYMOC monomers displayed essentially the same hybridization pattern and relative intensities as the control array made with the standard 5'-MeNPOC monomers.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

---

What is claimed is:

1. A method of protecting and deprotecting a reactive group in a compound, comprising:
   coupling the reactive group with a second compound of the formula Ar—C($R_1$)($R_2$)—O—C(O)—X, wherein:
   Ar is an optionally substituted fused polycyclic aryl or heteroaromatic group or a vinylogously substituted species of the foregoing;
   $R_1$ and $R_2$ are independently H, optionally substituted alkyl, alkenyl or alkynyl, or optionally substituted aryl or heteroaromatic group or a vinylogously substituted derivative of the foregoing; and
   X is a leaving group;
   provided that when Ar is 1-pyrenyl and $R_1$ and $R_2$ are H, the reactive group being protected is not an amine, to provide a protected compound with its reactive group protected by linkage to Ar—C($R_1$)($R_2$)—O—C(O)—; and
   irradiating the protected compound to provide a deprotected compound.

2. The method of claim 1, wherein Ar is independently 1-pyrenyl or 9-anthracenyl, $R_1$ is hydrogen and $R_2$ is independently hydrogen, methyl, substituted phenyl, 9-anthracenyl or 1-pyrenyl.

3. A method of protecting and deprotecting a reactive group in a compound, comprising:
   coupling the reactive group with a second compound of the formula Ar—C($R_1$)($R_2$)—X, wherein:
   Ar is an optionally substituted fused polycyclic aryl or heteroaromatic group or a vinylogously substituted species of the foregoing;
   $R_1$ and $R_2$ are independently H, optionally substituted alkyl, alkenyl or alkynyl, or optionally substituted aryl or heteroaromatic group or a vinylogously substituted derivative of the foregoing; and
   X is a leaving group, to provide a protected compound with its reactive group protected by linkage to Ar—C($R_1$)($R_2$)—O—C(O)—; and
   irradiating the protected compound to provide a deprotected compound.

4. The method of claim 3, wherein Ar is independently 1-pyrenyl or 9-anthracenyl, $R_1$ is hydrogen and $R_2$ is independently hydrogen, methyl, substituted phenyl, 9-anthracenyl or 1-pyrenyl.

5. The method of claim 4, wherein Ar is 1-pyrenyl and $R_1$ and $R_2$ are hydrogen.

6. The method of claim 4, wherein Ar is 9-anthracenyl, $R_1$ is hydrogen and $R_2$ is hydrogen.

7. The method of claim 3, wherein the compound is a ribonucleoside, deoxyribonucleoside or 2'-O-methylribonucleoside.

8. The method of claim 7, wherein the deoxyribonucleoside is linked to the Ar—C($R_1$)($R_2$)—O—C(O)— group via a 3' or 5'-OH.

9. The method of claim 3, wherein the Ar—C($R_1$)($R_2$)—O—C(O)— group is removed by irradiation with light.

10. The method of claim 9, wherein the wavelength is greater than 340 nm.

11. The method of claim 10, wherein the wavelength is about 365 nm.

\* \* \* \* \*